(12) United States Patent
Carranza et al.

(10) Patent No.: US 12,218,459 B2
(45) Date of Patent: Feb. 4, 2025

(54) SURGICAL INSTRUMENT WITH REMOVABLE CABLE AND ASSOCIATED COUPLINGS

(71) Applicant: Cilag GmbH International, Zug (CH)

(72) Inventors: Robert N. Carranza, Milford, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 315 days.

(21) Appl. No.: 17/854,166

(22) Filed: Jun. 30, 2022

(65) Prior Publication Data

US 2024/0006810 A1 Jan. 4, 2024

(51) Int. Cl.
| | | |
|---|---|---|
| *H01R 13/627* | (2006.01) | |
| *A61B 17/00* | (2006.01) | |
| *H01R 13/625* | (2006.01) | |
| *H01R 43/00* | (2006.01) | |

(52) U.S. Cl.
CPC ......... *H01R 13/6276* (2013.01); *A61B 17/00* (2013.01); *H01R 13/625* (2013.01); *H01R 43/002* (2013.01); *A61B 2017/00477* (2013.01); *H01R 2201/12* (2013.01)

(58) Field of Classification Search
CPC .......... A61B 18/14; A61B 2018/00178; A61B 17/00; A61B 2017/00477; H01R 13/6277; H01R 13/6276; H01R 13/625; H01R 43/002; H01R 2201/12
See application file for complete search history.

(56) References Cited

U.S. PATENT DOCUMENTS

| | | | |
|---|---|---|---|
| 5,014,379 | A | 5/1991 | Hull et al. |
| 5,057,119 | A | 10/1991 | Clark et al. |
| 7,316,424 | B2 | 1/2008 | Kardeis et al. |
| 7,354,440 | B2 | 4/2008 | Truckai et al. |
| 7,381,209 | B2 | 6/2008 | Truckai et al. |
| 8,061,014 | B2 | 11/2011 | Smith et al. |
| 8,663,220 | B2 | 3/2014 | Wiener et al. |
| 8,820,605 | B2 | 9/2014 | Shelton, IV |
| 9,125,662 | B2 | 9/2015 | Shelton, IV |
| 9,314,308 | B2 | 4/2016 | Parihar et al. |

(Continued)

FOREIGN PATENT DOCUMENTS

| | | | | |
|---|---|---|---|---|
| AU | 2013280951 A1 | * | 1/2015 | ........... A61B 17/295 |
| CA | 2495968 C | * | 11/2013 | ........... A61B 18/042 |

(Continued)

OTHER PUBLICATIONS

Non-Provisional U.S. Appl. No. 17/854,050; and.

(Continued)

*Primary Examiner* — Jean F Duverne
(74) *Attorney, Agent, or Firm* — Frost Brown Todd LLP

(57) ABSTRACT

A surgical device and method of processing includes a cable and a first adapter. The adapter includes a body, an electrical contact connected to the cable, and an engagement assembly. The engagement assembly includes a latch coupling or a communication coupling. The latch coupling is movable between a locked and an unlocked position and includes a catch member. The communication coupling is configured to be resiliently biased into engagement between the electrical contact and an instrument or generator.

20 Claims, 9 Drawing Sheets

(56) References Cited

U.S. PATENT DOCUMENTS

| | | |
|---|---|---|
| 9,421,060 B2 | 8/2016 | Monson et al. |
| 9,872,696 B2 | 1/2018 | Smith et al. |
| 9,949,785 B2 | 4/2018 | Price et al. |
| 10,426,508 B2 | 10/2019 | Smith et al. |
| 10,624,709 B2 | 4/2020 | Remm |
| 10,660,695 B2 | 5/2020 | Madan et al. |
| 10,835,307 B2 | 11/2020 | Shelton, IV et al. |
| 10,892,995 B2 | 1/2021 | Shelton, IV et al. |
| 11,229,471 B2 | 1/2022 | Shelton, IV et al. |
| 11,229,472 B2 | 1/2022 | Shelton, IV et al. |
| 11,259,830 B2 | 3/2022 | Nott et al. |
| 11,291,495 B2 | 4/2022 | Yates et al. |
| 11,364,075 B2 | 6/2022 | Yates et al. |
| 11,419,667 B2 | 8/2022 | Messerly et al. |
| 11,589,888 B2 | 2/2023 | Shelton, IV et al. |
| 11,690,642 B2 | 7/2023 | Black et al. |
| 2006/0079874 A1 | 4/2006 | Faller et al. |
| 2007/0191713 A1 | 8/2007 | Eichmann et al. |
| 2008/0200940 A1 | 8/2008 | Eichmann et al. |
| 2009/0171147 A1 | 7/2009 | Lee et al. |
| 2012/0292367 A1 | 11/2012 | Morgan et al. |
| 2019/0261991 A1* | 8/2019 | Beckman ............ A61B 17/115 |
| 2021/0346086 A1 | 11/2021 | Hase |
| 2024/0000474 A1 | 1/2024 | Shelton, IV et al. |
| 2024/0000475 A1 | 1/2024 | Shelton, IV et al. |
| 2024/0000476 A1 | 1/2024 | Shelton, IV et al. |
| 2024/0000491 A1 | 1/2024 | Shelton, IV et al. |
| 2024/0000526 A1 | 1/2024 | Shelton, IV et al. |
| 2024/0001416 A1 | 1/2024 | Shelton, IV et al. |
| 2024/0003820 A1 | 1/2024 | Shelton, IV et al. |
| 2024/0006048 A1 | 1/2024 | Shelton, IV et al. |

FOREIGN PATENT DOCUMENTS

| | | |
|---|---|---|
| CN | 111920164 A | 11/2020 |
| EP | 3505076 A2 | 7/2019 |

OTHER PUBLICATIONS

Non-Provisional U.S. Appl. No. 17/854,641.
Anonymous: "pcb design—Detachable "debug" portion of PCB?—Electrical Engineering Stack Exchange," downloaded from https://electronics.stackexchange.com/questions/356423/detachable-debug-portion-of-pcb, retrieved on Nov. 22, 2023, XP093104291, 4 pgs.
International Search Report and Written Opinion dated Sep. 8, 2023 for Application No. PCT/IB2023/056598, 13 pgs.
International Search Report and Written Opinion dated Oct. 10, 2023 for Application No. PCT/IB2023/056599, 12 pgs.
International Search Report and Written Opinion dated Dec. 18, 2023 for Application No. PCT/IB2023/056602, 21 pgs.
U.S. Appl. No. 62/611,339, filed Dec. 28, 2017, by Shelton, IV et al., entitled "Robot Assisted Surgical Platform."
U.S. Appl. No. 62/611,340, filed Dec. 28, 2017, by Shelton, IV et al., entitled "Cloud-Based Medical Analytics."
U.S. Appl. No. 62/611,341, filed Dec. 28, 2017, by Shelton, IV et al., entitled "Interactive Surgical Platform."

* cited by examiner

SURGICAL INSTRUMENT WITH REMOVABLE CABLE AND ASSOCIATED COUPLINGS

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; U.S. Pat. No. 8,663,220, entitled "Ultrasonic Electrosurgical Instruments," issued Mar. 4, 2014, the disclosure of which is incorporated by reference herein, in its entirety; U.S. Pat. No. 10,835,307, entitled "Modular Battery Powered Handheld Surgical Instrument Containing Elongated Multi-Layered Shaft," issued Nov. 17, 2020, the disclosure of which is incorporated by reference herein, in its entirety; and U.S. Pat. No. 11,229,471, entitled "Modular Battery Powered Handheld Surgical Instrument with Selective Application of Energy Based on Tissue Characterization," issued Jan. 25, 2022, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," published on May 2, 2019, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, the disclosure of which is incorporated by reference herein, in its entirety.

Such instruments and robotic surgical systems may be further be incorporated into a surgical system for performing procedures in a surgical environment, such as surgical operating theaters or rooms in a healthcare facility. A sterile field is typically created around the patient and may include properly attired, scrubbed healthcare professions as well as desired furniture and/or fixtures. Examples of such surgical systems and associated features are disclosed in U.S. Pat. Pub. No. 2019/0201046, entitled "Method for Controlling Smart Energy Devices," published on Jul. 4, 2019, the disclosure of which is incorporated by reference herein, in its entirety; U.S. Pat. Pub. No. 2019/0201080, entitled "Ultrasonic Energy Device Which Varies Pressure Applied by Clamp Arm to Provide Threshold Control Pressure at a Cut Progression Location," published on Jul. 4, 2019, the disclosure of which is incorporated by reference herein, in its entirety; U.S. Pat. Pub. No. 2019/0201091, entitled "Radio Frequency Energy Device for Delivering Combined Electrical Signals," published Jul. 4, 2019, the disclosure of which is incorporated by reference herein, in its entirety; U.S. Pat. Pub. No. 2019/0274717, entitled "Methods for Controlling Temperature in Ultrasonic Device," published Sep. 12, 2019, the disclosure of which is incorporated by reference herein, in its entirety; and U.S. Pat. Pub. No. 2019/0207857, entitled "Surgical Network Determination of Prioritization of Communication, Interaction, or Processing Based on System or Device Needs," published Jul. 4, 2019, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a cross-sectional view of the cable adapter of FIG. 9 taken along section line 9A-9A of FIG. 9;

Figure 1:
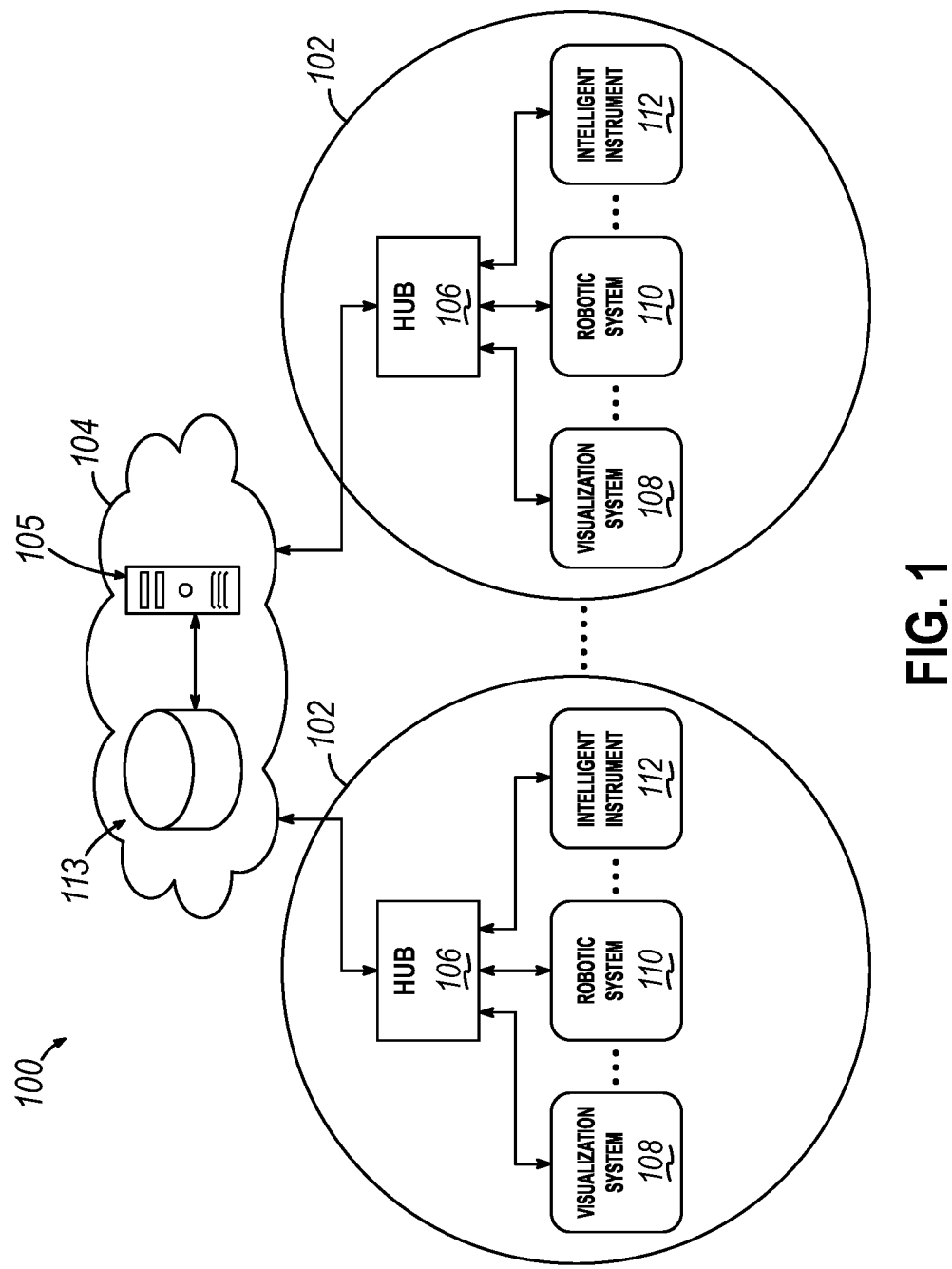
FIG. 1 depicts a block diagram of an example a computer-implemented interactive surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. Example of a Surgical System

With respect to FIG. 1, a computer-implemented interactive surgical system (100) includes one or more surgical systems (102) and a cloud-based system (e.g., a cloud (104) that may include a remote server (113) coupled to a storage device (105)). Each surgical system (102) of the present example includes at least one surgical hub (106) in communication with cloud (104) that may include a remote server (113). In one example, as illustrated in FIG. 1, surgical system (102) includes a visualization system (108), a robotic system (110), and a handheld intelligent surgical instrument (112), which are configured to communicate with one another and/or hub (106). In some aspects, a surgical system (102) may include an M number of hubs (106), an N number of visualization systems (108), an O number of robotic systems (110), and a P number of handheld intelligent surgical instruments (112), where M, N, O, and P are integers greater than or equal to one. In any case, any suitable combination of features provided below may be incorporated into an exemplary surgical system, such as surgical system (100), and used in the surgical theater in order to perform a desired surgical procedure as would be apparent to one skilled in the art in view of the teachings herein.

Figure 2:
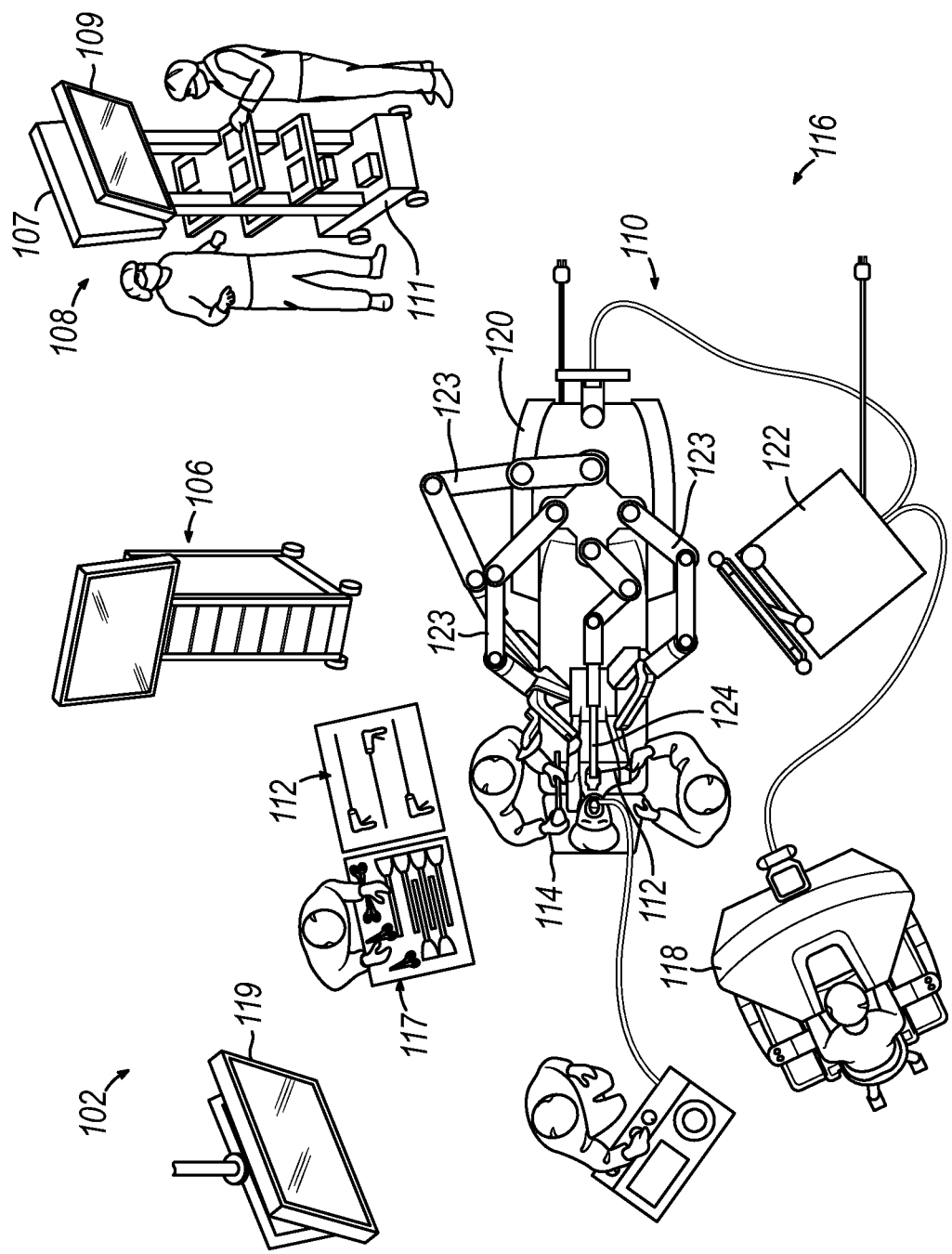
FIG. 2 depicts a top schematic view of an example of a surgical system for performing a surgical procedure in an operating room of a healthcare facility.

FIG. 2 depicts an example of a surgical system (102) being used to perform a surgical procedure on a patient who is lying down on an operating table (114) in a surgical operating room (116). A robotic system (110) is used in the surgical procedure as a part of surgical system (102). Robotic system (110) includes a surgeon's console (118), a patient side cart (120) (surgical robot), and a surgical robotic hub (122). Patient side cart (120) can manipulate at least one removably coupled surgical tool (117) with any one of a plurality of surgical arms (123) through a minimally invasive incision in the body of the patient while the surgeon views the surgical site through console (118). An image of the surgical site can be obtained by a medical imaging device (124), which can be manipulated by patient side cart (120) to orient imaging device (124). Robotic hub (122) can be used to process the images of the surgical site for subsequent display to the surgeon through console (118).

Other types of robotic systems can be readily adapted for use with surgical system (102). Various examples of robotic systems and surgical tools that are suitable for use with the present disclosure are described in U.S. Provisional Patent Application Ser. No. 62/611,339, entitled "Robot Assisted Surgical Platform," filed Dec. 28, 2017, the disclosure of which is herein incorporated by reference in its entirety.

Various examples of cloud-based analytics that are performed by cloud (104, and are suitable for use with the present disclosure, are described in U.S. Provisional Patent Application Ser. No. 62/611,340, entitled Cloud-Based Medical Analytics," filed Dec. 28, 2017, the disclosure of which is herein incorporated by reference in its entirety.

In various aspects, imaging device (124) includes at least one image sensor and one or more optical components. Suitable image sensors include, but are not limited to, Charge-Coupled Device (CCD) sensors and Complementary Metal-Oxide Semiconductor (CMOS) sensors. In various aspects, imaging device (124) is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. Some aspects of spectral and multi-spectral imaging are described in greater detail under the heading "Advanced Imaging Acquisition Module" in U.S. Provisional Patent Application Ser. No. 62/611,341, entitled "Interactive Surgical Platform," filed Dec. 28, 2017, the disclosure of which is herein incorporated by reference in its entirety.

Strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In addition to the introduction of any features of surgical system (100), furniture, or fixtures into the sterile field requiring sterilization, additional complications may result from removal of these features from the sterile field, particularly when such features may have contacted, or presumed to have contacted, the patient, including any tissues and/or fluids associated with the surgical procedure. Such contamination of these features from the patient often requires special consideration during or after the surgical procedure, particularly when processing these features for disposal, reuse, or remanufacturing as desired. In one example, surgical system (100) and/or healthcare professionals associated with the surgical procedure may be specifically equipped to address such processing as discussed below in greater detail.

As illustrated in FIG. 2, a primary display (119) is positioned in the sterile field to be visible to an operator at operating table (114). In addition, a visualization tower (111) is positioned outside the sterile field. Visualization tower (111) includes a first non-sterile display (107) and a second non-sterile display (109), which face away from each other. Visualization system (108), guided by hub (106), is configured to utilize displays (107, 109, 119) to coordinate information flow to operators inside and outside the sterile field. For example, hub (106) may cause visualization system (108) to display a snapshot of a surgical site, as recorded by imaging device (124), on a non-sterile display (107) or (109), while maintaining a live feed of the surgical site on the primary display (119). The snapshot on non-sterile display (107) or display (109) can permit a non-sterile operator to perform a diagnostic step relevant to the surgical procedure, for example.

In one aspect, hub (106) is also configured to route a diagnostic input or feedback entered by a non-sterile operator at visualization tower (111) to primary display (119) within the sterile field, where it can be viewed by a sterile operator at the operating table. In one example, the input can be in the form of a modification to the snapshot displayed on non-sterile display (107) or display (109), which can be routed to primary display (119) by hub (106).

Referring to FIG. 2, a surgical instrument (112) is being used in the surgical procedure as part of surgical system (102). Hub (106) is also configured to coordinate information flow to a display of the surgical instrument (112) such as in, for example, U.S. Provisional Patent Application Ser. No. 62/611,341, entitled "Interactive Surgical Platform," filed Dec. 28, 2017, the disclosure of which is herein incorporated by reference in its entirety. A diagnostic input or feedback entered by a non-sterile operator at visualization tower (111) can be routed by hub (106) to surgical instrument display (115) within the sterile field, where it can be viewed by the operator of surgical instrument (112). Example surgical instruments that are suitable for use with surgical system (102) are described under the heading "Surgical Instrument Hardware" and in U.S. Provisional Patent Application Ser. No. 62/611,341, entitled "Interactive Surgical Platform," filed Dec. 28, 2017, the disclosure of which is herein incorporated by reference in its entirety, for example.

Figure 3:
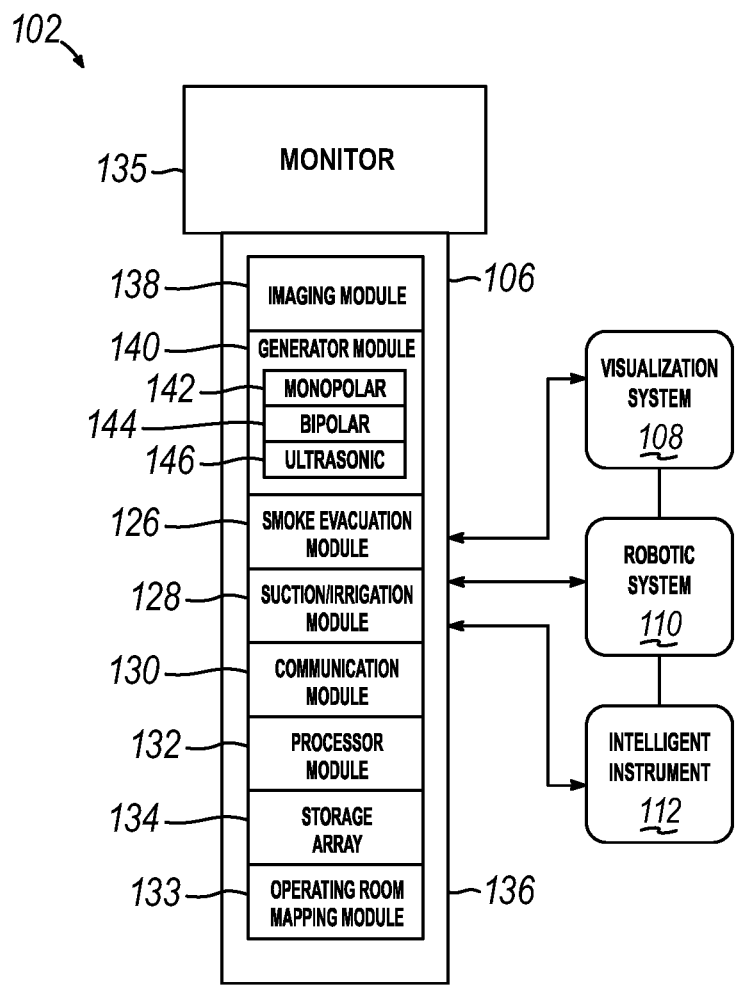
FIG. 3 depicts a side schematic view of an example of a surgical hub of the surgical system of FIG. 2.

Referring now to FIG. 3, a hub (106) is depicted in communication with a visualization system (108), a robotic system (110), and a handheld intelligent surgical instrument (112). Hub (106) includes a hub display (135), an imaging module (138), a generator module (140), a communication module (130), a processor module (132), and a storage array (134). In certain aspects, as illustrated in FIG. 3, hub (106) further includes a smoke evacuation module (126), a suction/irrigation module (128), and/or an operating room mapping module (133).

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure (136) offers a unified environment for managing the power, data, and fluid lines, which reduces the frequency of entanglement between such lines.

Figure 4:
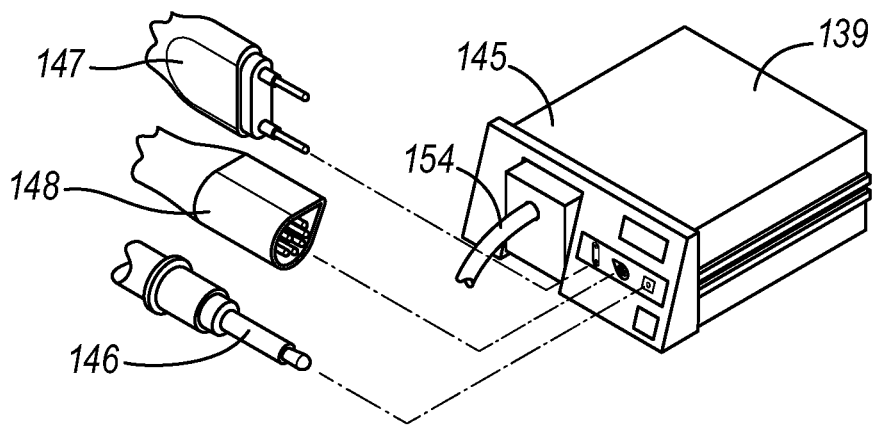
FIG. 4 depicts a perspective view of a combination generator module with bipolar, ultrasonic, and monopolar contacts of the surgical system of FIG. 2.

Referring to FIGS. 3-4, aspects of the present disclosure are presented for a hub modular enclosure (136) that allows the modular integration of a generator module (140), a smoke evacuation module (126), and a suction/irrigation module (128). Hub modular enclosure (136) further facilitates interactive communication between modules (140, 126, 128). As shown in FIG. 4, generator module (140) can be a generator module with integrated monopolar, bipolar, and ultrasonic components supported in a single housing unit (139) slidably insertable into hub modular enclosure (136). As illustrated in FIG. 4, generator module (140) can be configured to connect to a monopolar device (146), a bipolar device (147), and an ultrasonic device (148). Alternatively, generator module (140) may comprise a series of monopolar, bipolar, and/or ultrasonic generator modules that interact through hub modular enclosure (136). Hub modular enclosure (136) can be configured to facilitate the insertion of multiple generators and interactive communication between the generators docked into the hub modular enclosure (136) so that the generators would act as a single generator.

Figure 5:
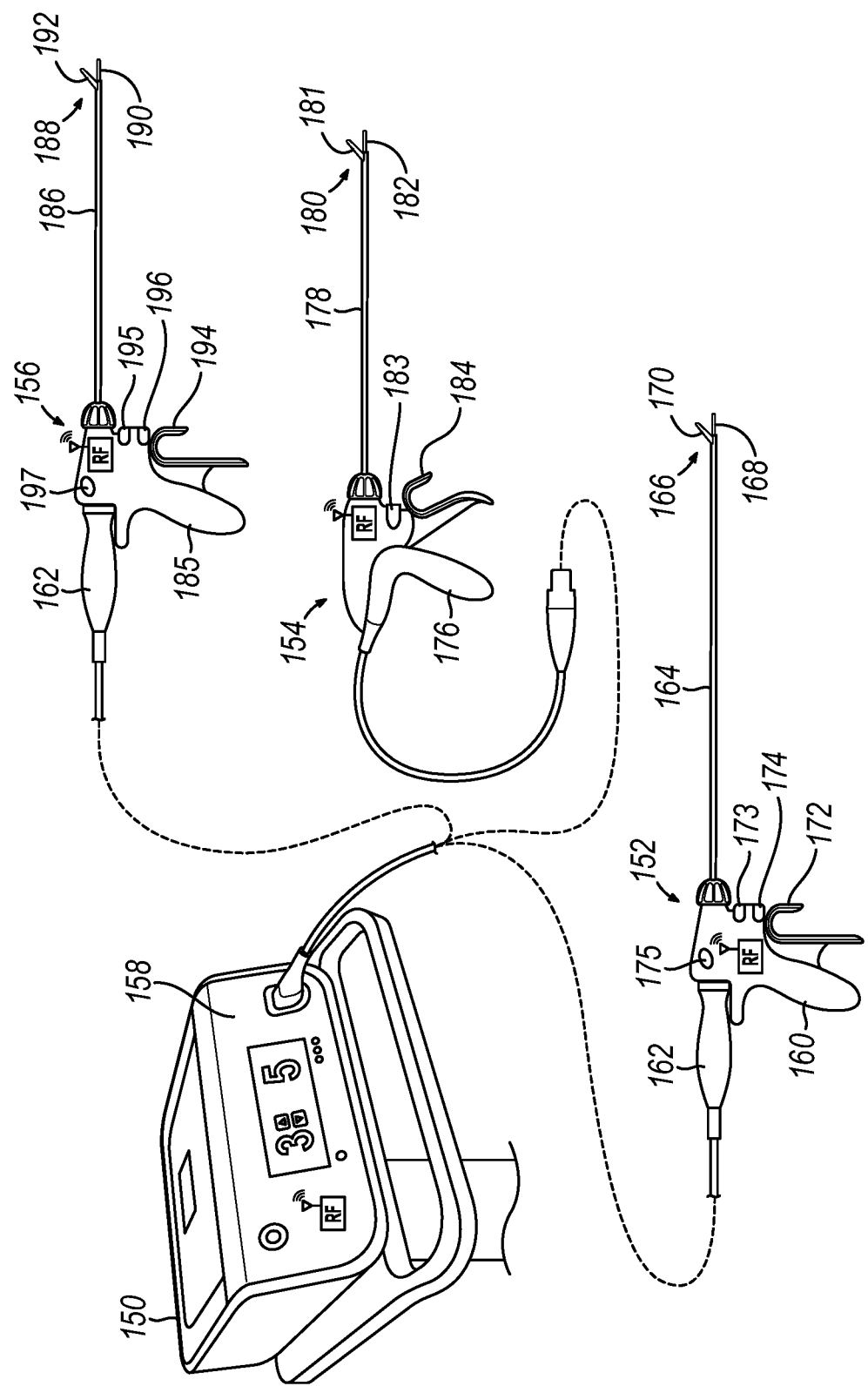
FIG. 5 depicts a side schematic view of an exemplary generator and various examples of surgical instruments for use with the surgical system of FIG. 2.

FIG. 5 illustrates one form of a generator (150) and various surgical instruments (152, 154, 156) usable therewith, where surgical instrument (152) is an ultrasonic surgical instrument (152), surgical instrument (154) is an RF electrosurgical instrument (154), and multifunction surgical instrument (156) is a combination ultrasonic/RF electrosurgical instrument (156). Generator (150) is configurable for use with a variety of surgical instruments. According to various forms, generator (150) may be configurable for use with different surgical instruments of different types including, for example, ultrasonic surgical instruments (152), RF electrosurgical instruments (154), and multifunction surgical instruments (156) that integrate RF and ultrasonic energies delivered simultaneously from generator (150). Although generator (150) of the present example in FIG. 5 is shown separate from surgical instruments (152, 154, 156), generator (150) may alternatively be formed integrally with any of surgical instruments (152, 154, 156) to form a unitary surgical system. Generator (150) comprises an input device (158) located on a front panel of generator (150) console. Input device (158) may comprise any suitable device that generates signals suitable for programming the operation of generator (150). Generator (150) may be configured for wired or wireless communication.

Generator (150) of the present example is configured to drive multiple surgical instruments (152, 154, 156). One example of such surgical instrument is ultrasonic surgical instrument (152) and comprises a handpiece (160), an ultrasonic transducer 162, a shaft assembly (164), and an end effector (166). End effector (166) includes an ultrasonic blade (168) acoustically coupled to ultrasonic transducer (162) and a clamp arm (170). Handpiece (160) has a trigger (172) to operate clamp arm (170) and a combination of toggle buttons (173, 174, 175) to energize and drive ultrasonic blade (168) or other function. Toggle buttons (173, 174, 175) can be configured to energize ultrasonic transducer (162) with generator (150).

Generator (150) also is configured to drive another example of surgical instrument (154). RF electrosurgical instrument (154) includes a handpiece (176), a shaft assembly (178), and an end effector (180). End effector (180) includes electrodes in clamp arms (181, 182) and return through an electrical conductor portion of shaft assembly (178). Electrodes are coupled to and energized by a bipolar energy source within generator (150). Handpiece (176) includes a trigger (183) to operate clamp arms (181, 182) and an energy button (184) to actuate an energy switch to energize electrodes in end effector (180).

Generator (150) also is configured to drive multifunction surgical instrument (156). Multifunction surgical instrument (156) includes a handpiece (185), a shaft assembly (186), and an end effector (188). End effector (188) has an ultrasonic blade (190) and a clamp arm (192). Ultrasonic blade (190) is acoustically coupled to ultrasonic transducer (162). Handpiece (185) has a trigger (194) to operate clamp arm (192) and a combination of toggle buttons (195, 196, 197) to energize and drive ultrasonic blade (190) or other function. Toggle buttons (195, 196, 197) can be configured to energize ultrasonic transducer (162) with generator (150) and energize ultrasonic blade (190) with a bipolar energy source also contained within generator (150). It will be appreciated that handpieces (160, 176, 185) may be replaced with a robotically controlled instrument for incorporating one or more aspects of surgical instruments (152, 154, 156). Accordingly, the term "handpiece" should not be limited to this context and to handheld use.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions, all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device. Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

II. Surgical Instrument with Removable Cable and Associated Couplings

Figure 6:
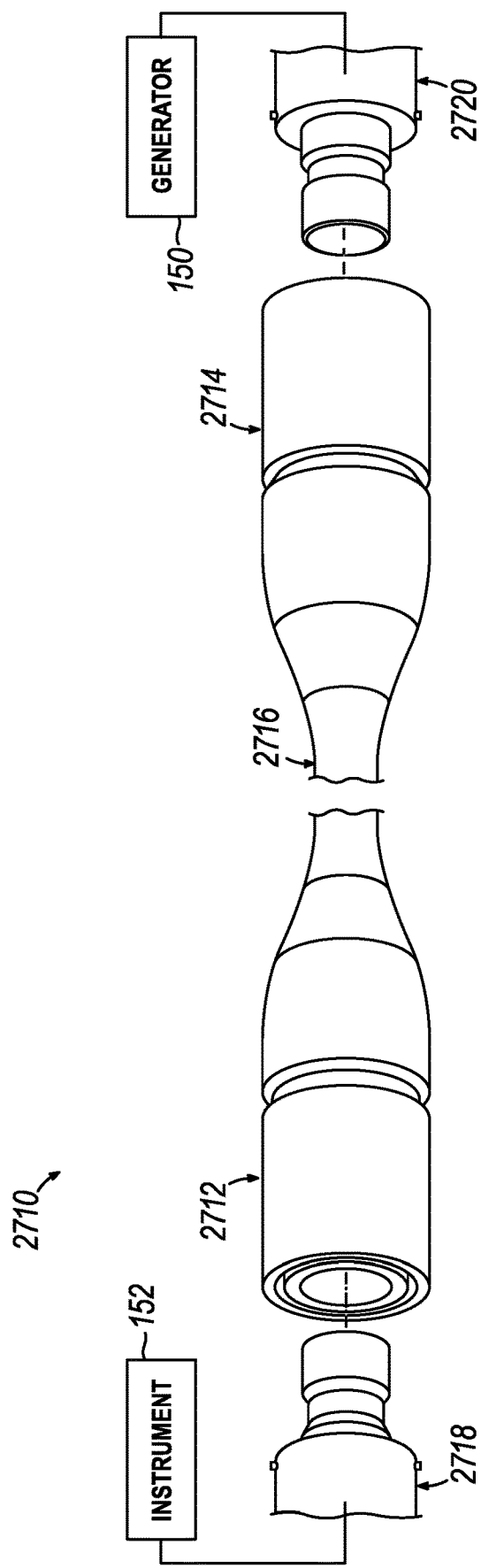
FIG. 6 depicts a perspective view of an exemplary cable assembly connected between a medical device and a generator for use with the surgical system of FIG. 2.

FIG. 6 illustrates an exemplary surgical device as a first example of a cable assembly (2710) used to connect to a medical device, such as surgical instrument (152), to a generator, such as generator (150) for transmitting electrical power and electrical communication signals. Cable assembly (2710) includes at least one cable adapter (2712, 2714) for connecting to at least one device, but may also include multiple adapters (2712, 2714) for connecting to multiple devices as shown in the present example and a cable (2716) which collectively act as a jumper between devices. Surgical instrument (152) may be reusable as a whole or may be disassembled to reuse only a portion of cable assembly (2710). Reusable portions may be determined based on the cost of particular portions, the ease of removing and replacing particular portions, the environmental impact of not reusing particular portions, or the visual aesthetics of particular portions. Surgical instrument (152) may also be disassembled for cleaning and sterilization purposes. Such sterilization purposes may include autoclaving and ethylene oxide sterilization of either a select portion of surgical instrument (125) or an entirety surgical instrument (152). Surgical instrument (152) may help to alleviate the cost of procedures by allowing for a reusable electrical conduit rather than using a traditional one-time use disposable electrical conduit. Cable adapters (2712, 2714) and cable (2716) may also shield the electrical conduits from external signals which would affect the performance of surgical instrument (152) and/or generator (150) when conducting electrical communications. While cable assembly (2710) is shown more particularly in the present example as connecting surgical instrument (152) to generator (150) respectively via an instrument adapter (2718) and a generator adapter (2720), cable assembly (2710) may alternatively connect any such devices and/or generators discussed herein such that the invention is not intended to be unnecessarily limited to use with surgical instrument (152) and generator (150).

Figure 7:
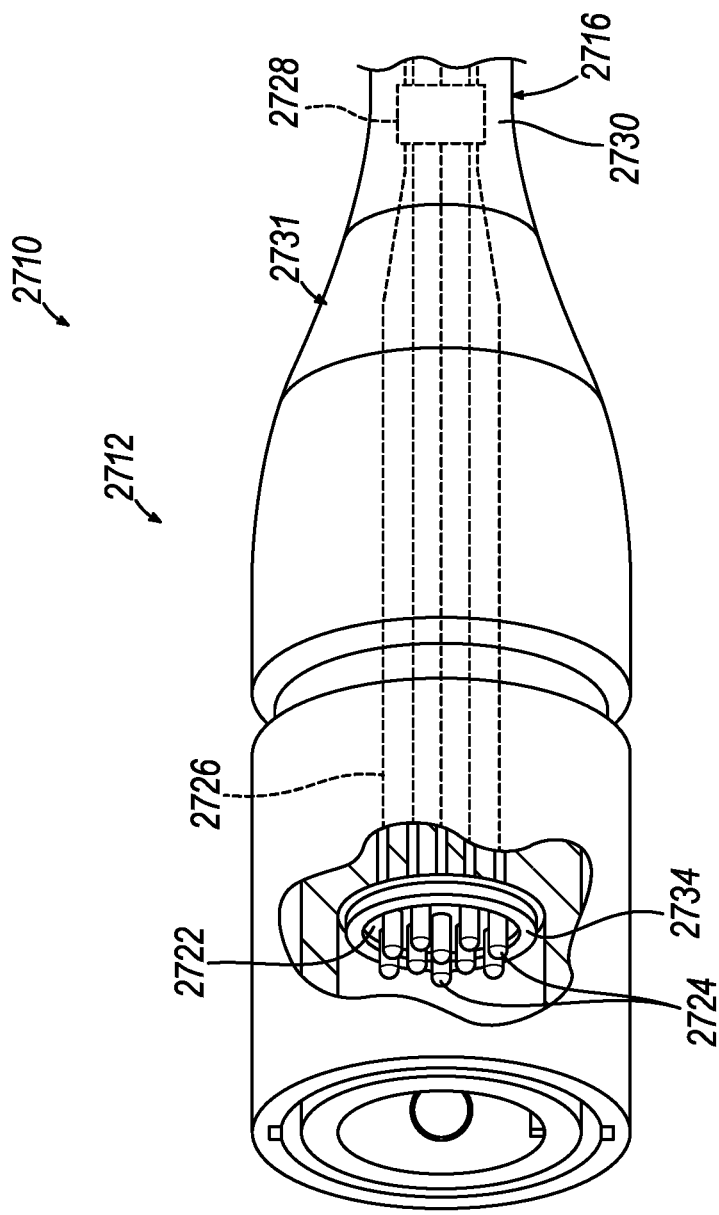
FIG. 7 depicts an enlarged, partially cutaway, perspective view of a cable adapter of the cable assembly of FIG. 6.

FIG. 7 shows cable adapter (2712) having a terminal seat (2722) with a plurality of electrical contacts (2724) supported thereon. Each electrical contact (2724) in the present example connects to an electrical conduit (2726), which extends to an integrated circuit (2728). As further shown in the present example, integrated circuit (2728) is removably connected to a cable body (2730) of cable (2716) although integrated circuit (2778) in another example may be integrated into any one of adapters (2712, 2714) (see FIG. 6) or even not included at all in other examples. Integrated circuit (2778) is configured to track various parameters and/or metrics of past use of surgical instrument (152), cable assembly (2710), and/or generator (150).

A strain relief (2731) is coupled between cable adapter (2712) and cable body (2730) and configured to inhibit damage to cable body (2730) and/or electrical conduits (2726) when cable assembly (2710) is pulled and/or bent with a damaging force or a damaging angle. In one example, strain relief (2731) may be adhered to cable body (2730) or may simply surround cable body (2730) similar to a shroud. Strain relief (2731) may be permanently or removably secured to cable adapter (2712) and/or cable body (2730) for replacement. Strain relief (2731) may vary in size in order to accommodate differing diameters and to offer more or less strain protection as desired.

At least one electrical conduit (2726), such as a wire, extends from integrated circuit (2728) and traverses cable body (2730) to opposing cable adapter (2714) (see FIG. 6) for connection with generator (150) (see FIG. 6). By way of example, electrical contacts (2724) may be externally coated or made of a corrosion resistant material such as gold or dielectric grease to prohibit corrosion and to promote electrical communication. Electrical contacts (2724) and electrical conduits (2726) may be shielded by adapters (2712, 2714, 2718, 2720) as applicable to form a female type fitting, such as in cable adapters (2712, 2714) of the present example, or may be external to adapters (2712, 2714, 2718, 2720) to form a male type fitting, such as in instrument and generator adapters (2718, 2720).

Figure 8:
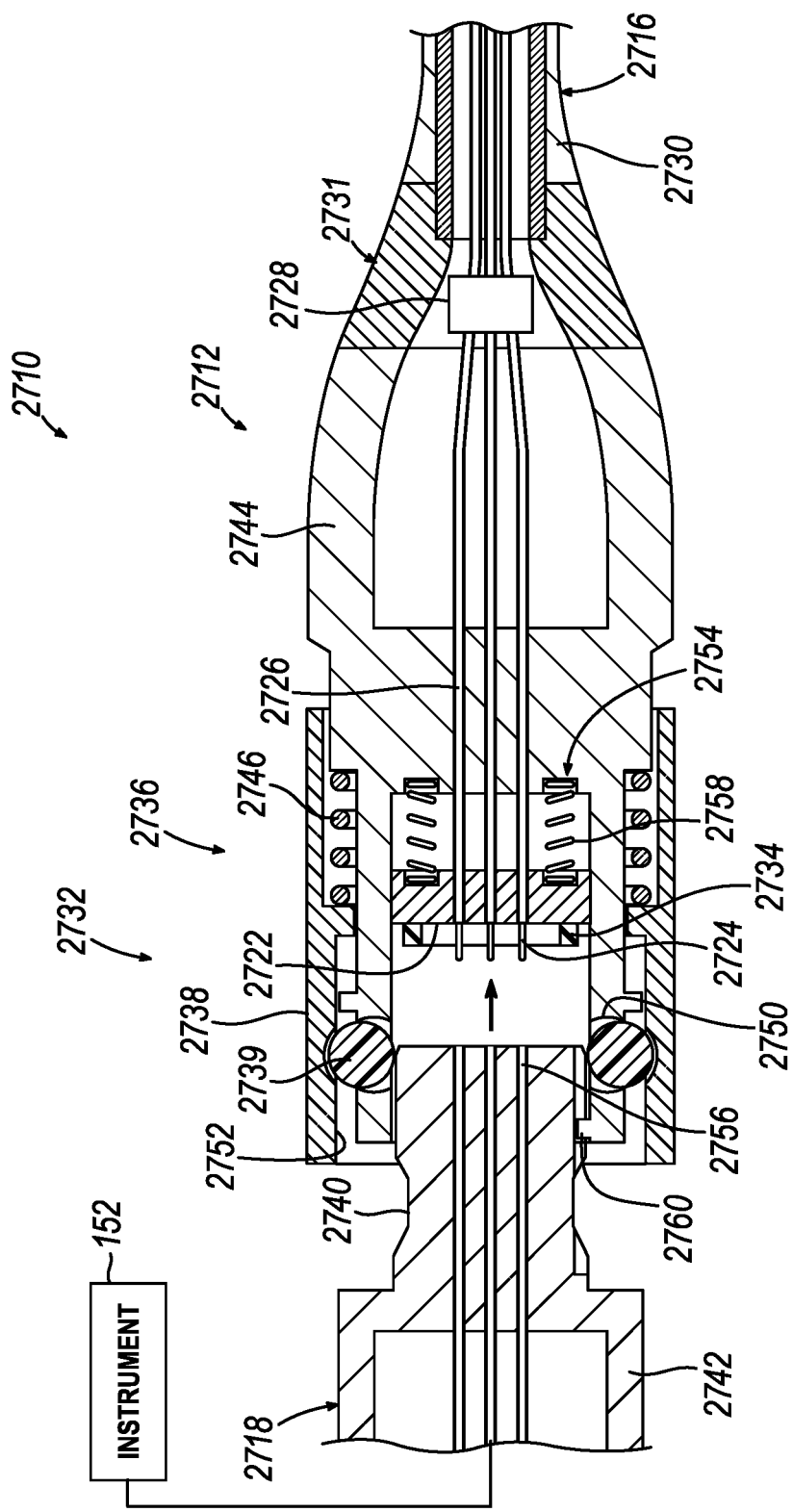
FIG. 8 depicts an enlarged, cross-sectional view of the cable adapter of FIG. 7 taken along a centerline thereof receiving an exemplary instrument adapter of the medical device of FIG. 6 in an uncoupled position.
Figure 9:
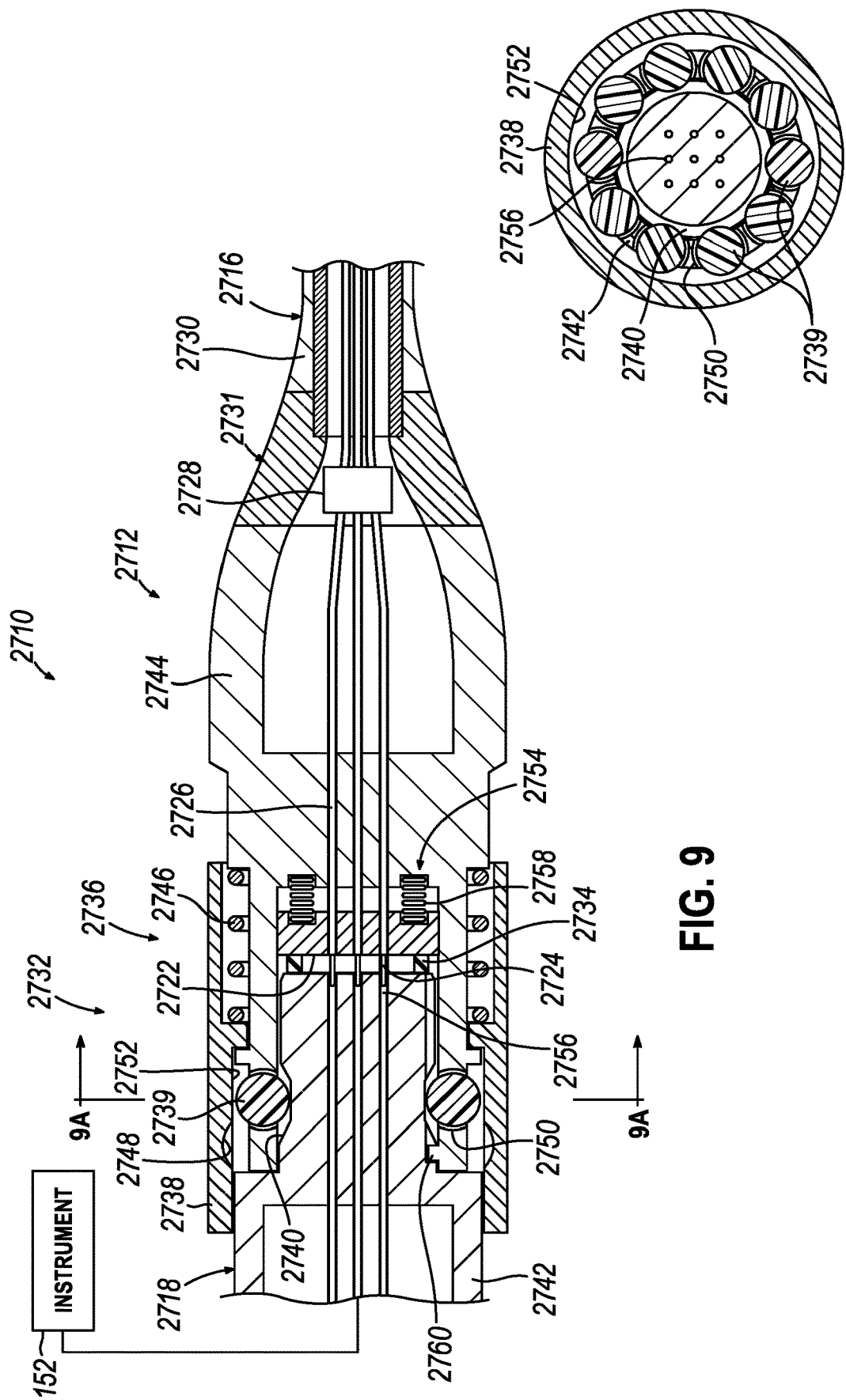
FIG. 9 depicts the enlarged, cross-sectional view of the cable adapter similar to FIG. 8, but showing the instrument adapter received by the cable adapter from a partially coupled, unlocked position to a fully coupled, locked position.

To this end, with respect to FIG. 8, cable adapter (2712) and instrument adapter (2718) define an electrical coupling (2732), whereas cable adapter (2714) (see FIG. 6) and generator adapter (2720) (see FIG. 6) similarly define another such electrical coupling (2732), albeit on opposing ends of cable (2716). Cable adapter (2712) of electrical coupling (2732) includes a seal (2734) configured to inhibit ingress of foreign materials into electrical coupling (2732) when coupled as shown in FIG. 9. Seal (2734) may also be located around all electrical contacts (2724) within electrical coupling (2732) to inhibit the ingress of foreign materials to electrical contacts (2724) when cable assembly (2710) is coupled to surgical instrument (152) (see FIG. 6) and/or generator (150) (see FIG. 6).

Referring to each of FIG. 8, FIG. 9, and FIG. 9A, electrical coupling (2732) includes a latch coupling (2736), which has a selectively translatable sleeve (2738), a plurality of catch members (2739), and an annular groove (2740). More particularly, annular groove (2740) is positioned on an instrument adapter body (2742) to surround a longitudinal axis of electrical coupling (2732), whereas catch members (2739) are angularly positioned about the longitudinal axis of electrical coupling (2732) surrounding the longitudinal axis about a majority of a circumference of a cable adapter body (2744) of cable adapter (2714). Catch members (2739) are further selectively movably secured to cable adapter body (2744). Sleeve (2738) is also movably secured to cable adapter body (2744) to radially surround the longitudinal axis selectively translate in the longitudinal direction.

To this end, sleeve (2738) of the present example is configured to move from the locked position, which mechanically couples cable adapter (2712) to instrument adapter (2718), to the unlocked position, which mechanically uncouples cable adapter (2712) from instrument adapter (2718). In the present example, sleeve (2738) is biased toward the locked position by a sleeve spring (2746) secured in compression between cable adapter body (2744) and sleeve (2738) thereby pushing sleeve (2738) toward the locked position.

In order to enable mechanical coupling and uncoupling from the unlocked position, sleeve (2738) further includes an inner annular recess (2748) positioned to longitudinally align with catch members (2739), which in the present example are more particularly shown as ball-bearings (2739). Cable adapter (2712) further includes at least one receptacle (2750) configured to retain ball-bearings (2739), although it will be appreciated that any member configured to be so retained, such as pins, may be similarly used. Receptacle (2750) longitudinally secures ball-bearings (2739), while simultaneously allowing for limited inner and outer radial movement and permitted by surrounding structures. For example, an inner sidewall (2752) generally urges ball-bearings (2739) radially inward when sleeve is not in the unlocked position; however, inner annular recess (2748) receives ball-bearings (2739) in the unlocked position to allow ball-bearings (2739) to move radially outward. Thus, with sleeve (2738) in the unlocked position, instrument adapter body (2742) urges ball-bearings (2739) radially outward into inner annular recess (2748) of sleeve (2738) upon insertion into cable adapter body (2744). Once annular groove (2740) longitudinally aligns with ball-bearings (2739) as instrument adapter (2718) and cable adapter (2712) are partially coupled, sleeve (2738) selectively returns to the locked position such that inner sidewall (2752) of sleeve (2738) urges ball-bearings (2739) radially inward toward annular groove (2740) in instrument adapter body (2742). Ball-bearings (2739) are effectively captured in annular groove (2740) between inner sidewall (2752) of sleeve (2738) and instrument adapter body (2742) such that instrument adapter (2718) and cable adapter (2712) are fully coupled in the locked position for communication along electrical conduits (2726).

While mechanically coupling instrument adapter body (2742) relative to cable adapter body (2744) generally inhibits inadvertent uncoupling of cable and instrument adapters (2712, 2718), electrical coupling (2732) of the present example further includes a communication coupling (2754) configured to urge direct engagement between electrical contacts (2724) on terminal seat (2722) of cable adapter (2712) and electrical contacts (2756) of instrument adapter (2718). By way of example, terminal seat (2722) of communication coupling (2754) with electrical contacts (2724) is resiliently biased away from cable body (2730) toward instrument adapter (2718) to promote engagement with electrical contacts (2756) in instrument adapter (2718). Communication coupling (2754) thereby allows the electrical contacts (2724) with terminal seat (2722) to longitudinally translate within a predetermined range, which in the present example is a longitudinal predetermined stroke, by pushing against cable adapter body (2744). On one end of the predetermined stroke with a seat spring (2758) in an extended state, electrical contacts (2724) with terminal seat (2722) are fully advanced at a distance away from cable (2716), prior to insertion of instrument adapter body (2742). At the other end of the predetermined stroke, with instrument adapter body (2742) coupled to cable adapter (2712) and seat spring (2758) in a retracted state, electrical contacts (2756) on instrument adapter body (2742) urge terminal seat (2722) toward cable (2716) such that seat spring (2758) is compressed between terminal seat (2722) and cable adapter body (2744). Seat spring (2758) will continue to push electrical contacts (2724) on terminal seat (2722) into adjoining electrical contacts (2756) of instrument adapter (2718) to promote engagement and electrical communication therebetween. In one example, in the event of uncoupling of cable adapter (2712) and instrument adapter (2718) while unlocking latch coupling (2736), seat spring may further aid in the separation of cable adapter (2712) and instrument adapter (2718).

In order to further aid alignment between cable adapter (2712) and instrument adapter (2718), cable adapter (2712) further includes an alignment feature, such as an alignment key (2760), for angularly aligning cable adapter (2712) and instrument adapter (2718) about the longitudinal axis relative to each other. Holding angular alignment will allow the respective electrical contacts (2724, 2756) to properly align as applicable and engage with one another to maintain engagement while coupling and during use of surgical instrument (152) (see FIG. 6).

While the above description is generally directed toward cable adapter (2712) and instrument adapter (2718), it will be appreciated that cable adapter (2714) and generator adapter (2720) are generally identical to cable adapter (2712) and instrument adapter (2718), respectively, unless otherwise described herein. The above description of cable adapter (2712) and instrument adapter (2718) thus similarly applies to cable adapter (2714) and generator adapter (2720) in the present example, although the invention should not be limited to cable adapter (2712) being like cable adapter (2714) and instrument adapter (2718) being like generator adapter (2720). It will be further appreciated that any adapters (2712, 2714, 2718, 2720) may be interchanged with related features on any devices as desired so long as adapters (2712, 2714, 2718, 2720) are configured to effectively mate for communication therebetween during use. In other words, in one example one or more instrument or generator adapters (2718, 2720) may be incorporated into cable assembly (2710) and/or one or more of cable adapters (2712, 2714) may be incorporated into surgical instrument (152) (see FIG. 6) and/or generator (150) (see FIG. 6). The invention is thus not intended to be limited to the particular arrangement of adapters (2712, 2714, 2718, 2720) as shown in the present example.

Figure 10:
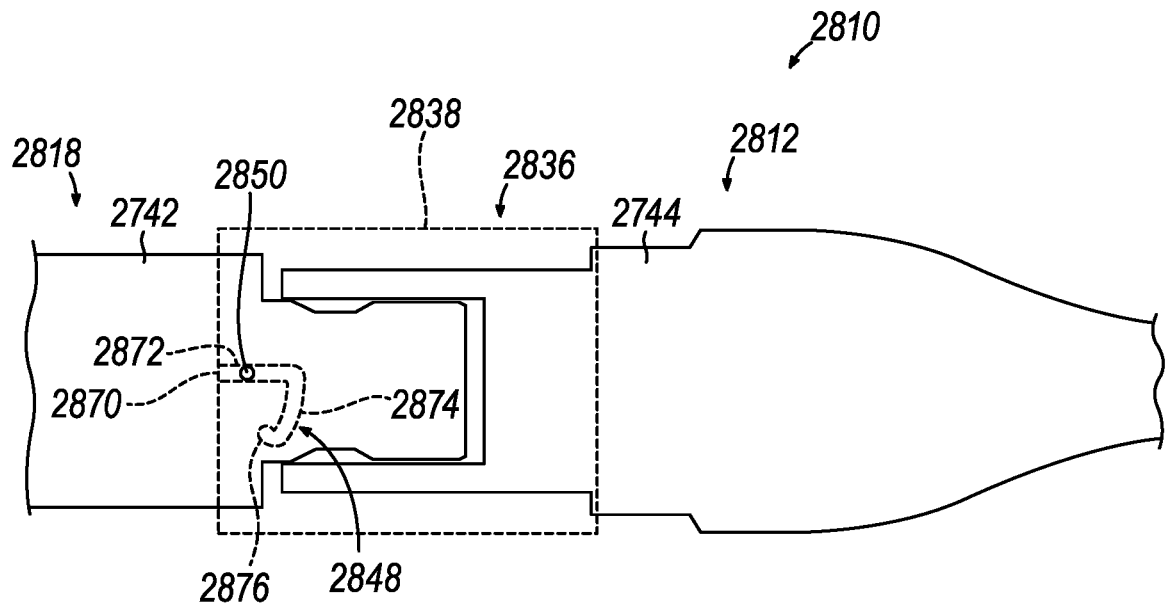
FIG. 10 depicts a side schematic view of another exemplary cable assembly receiving another exemplary instrument adapter of a medical device from an uncoupled position to a partially coupled, unlocked position.
Figure 11:
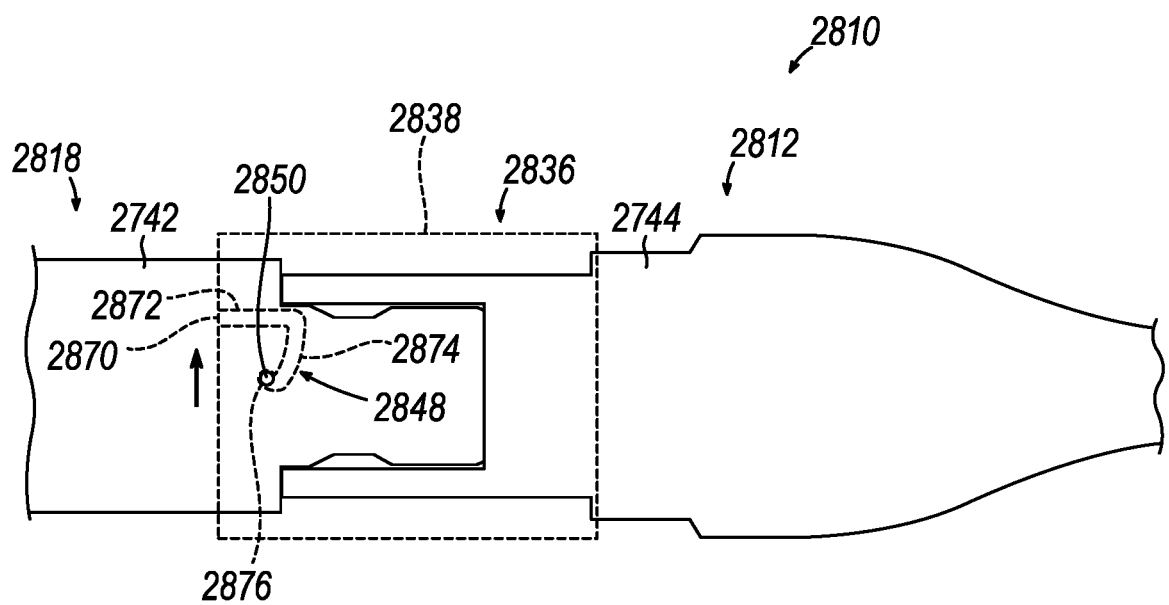
FIG. 11 depicts the side schematic view of the cable assembly and instrument adapters similar to FIG. 10, but showing the cable assembly and instrument adapters moved from the partially coupled, unlocked position of FIG. 10 to a fully coupled, locked position.

FIGS. 10 and 11 illustrate another exemplary cable assembly (2810) with a cable adapter (2812), an instrument adapter (2818), and an alternative example of a latch coupling (2836) having a rotatable sleeve (2838) for mechanically coupling instrument adapter body (2742) and cable adapter body (2744) together. In this respect, cable and instrument adapters (2812, 2818) are like cable and instrument adapters (2712, 2718) discussed above unless otherwise explicitly noted herein with like numbers indicating like features. More particularly, sleeve (2838) includes a bayonet slot (2848) extending radially therethrough and configured to receive an accompanying bayonet pin (2850) radially extending from instrument adapter body (2742). Sleeve (2838) with bayonet slot (2848) is configured to rotate relative to cable adapter body (2744), whereas bayonet pin (2850) rigidly extends from and is fixed relative to instrument adapter body (2742).

Bayonet slot (2848) more particularly includes an opening (2870), a longitudinally extending linear portion (2872), a longitudinally and angularly extending arcuate portion (2874), and a locking, terminal cavity (2876). Sleeve (2838) is rotatable about cable adapter body (2844) from a partially coupled, unlocked position with bayonet pin (2850) received through opening (2870) into linear portion (2872) as shown in FIG. 10 to a fully coupled, locked position with bayonet pin (2850) rotated through arcuate portion (2874) against an end of bayonet slot (2848) in terminal cavity (2876). Once bayonet pin (2850) reaches the rounded portion, a sleeve spring (2846) advances sleeve (2838) distally in relation to cable (2716) such that bayonet pin (2850) is captured terminal cavity (2876) to thereby secure cable adapter (2812) to instrument adapter (2818) in the locked position. In one example, as terminal cavity (2876) receives bayonet pin (2850), bayonet pin (2850) and sleeve (2838) collectively generate an audible noise and/or tactile feedback to indicate the locked position.

While the above description is generally directed toward cable adapter (2812) and instrument adapter (2818), it will be appreciated that adapters (2812, 2818) may be cooperatively interchanged or included together with any of adapters (2712, 2714, 2718, 2720) with related features on any devices as desired so long as adapters (2712, 2714, 2718, 2720) are configured to effectively mate for communication therebetween during use. Again, the invention is thus not intended to be limited to the particular arrangement of adapters (2812, 2818) as shown in the present example.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical device, comprising: (a) a cable configured to communicate an electrical energy therethrough, (b) a first adapter extending along a longitudinal axis from the cable and configured to releasably connect to at least one of an instrument adapter of a surgical instrument or a generator adapter of a generator, the first adapter including: (i) an adapter body, (ii) a first electrical contact electrically connected to the cable, and (iii) an engagement assembly, including: (A) a latch coupling having a latch portion selectively movable relative to the adapter body between a locked position and an unlocked position, wherein the latch portion includes at least lease one catch member angularly surrounding at least a majority of the longitudinal axis or a sleeve rotatable about the longitudinal axis, wherein the latch portion in the locked position is configured to capture the at least one of the instrument adapter or the generator adapter for retaining electrical connection between the first electrical contact and the at least one of the instrument adapter or the generator adapter, and wherein the latch portion in the unlocked position is configured to release the at least one of the instrument adapter or the generator adapter for uncoupling electrical connection between the first electrical contact and the at least one of the instrument adapter or the generator adapter, or (B) a communication coupling supported by the adapter body and configured to resiliently bias engagement between the first electrical contact and the at least one of the instrument adapter or the generator adapter for urging contact therebetween.

Example 2

The surgical device of Example 1, further comprising a surgical instrument having an instrument adapter or a generator having a generator adapter.

Example 3

The surgical device of any one or more of Examples 1 through 2, wherein the first adapter includes the latch coupling.

Example 4

The surgical device of any one or more of Examples 1 through 3, wherein the latch coupling includes the sleeve operatively connected to the adapter body, wherein the sleeve is configured to translate between the locked and unlocked positions.

Example 5

The surgical device of any one or more of Examples 1 through 4, wherein the latch coupling further includes a latch biasing element, wherein the latch biasing element resiliently biases the sleeve toward the locked position.

Example 6

The surgical device of any one or more of Examples 2 through 5, wherein the latch coupling further includes the at least one catch member positioned about the longitudinal axis and movable in a radial direction relative to the longitudinal axis and configured to longitudinally capture the at least one of the instrument adapter or the generator adapter in the locked position and further configured to longitudinally release the at least one of the instrument adapter or the generator adapter in the unlocked position.

Example 7

The surgical device of any one or more of Examples 1 through 6, wherein the at least one catch member includes a plurality of ball bearings.

Example 8

The surgical device of any one or more of Examples 1 through 7, wherein the latch coupling includes the sleeve operatively connected to the adapter body, wherein the sleeve is configured to rotate between the locked and unlocked positions.

Example 9

The surgical device of any one or more of Examples 1 through 8, wherein the latch coupling further includes a bayonet coupling having a bayonet slot, wherein the bayonet slot extends through at least one of the sleeve or the adapter body.

Example 10

The surgical device of Example 9, wherein the bayonet slot extends through the sleeve.

Example 11

The surgical device of any one or more of Examples 1 through 10, wherein the latch coupling further includes a latch biasing element, wherein the latch biasing element resiliently biases the sleeve toward the locked position.

Example 12

The surgical device of any one or more of Examples 1 through 11, wherein the first adapter includes the communication coupling.

Example 13

The surgical device of any one or more of Examples 1 through 12, wherein the first adapter includes the communication coupling.

Example 14

The surgical device of any one or more of Examples 1 through 13, wherein the communication coupling has a biasing element supported by the adapter body and configured to resiliently bias engagement between the first electrical contact and the at least one of the instrument adapter or the generator adapter for urging contact therebetween.

Example 15

The surgical device of any one or more of Examples 1 through 14, wherein the communication coupling further includes a seat operatively connected to the adapter body and configured to longitudinally move from an extended position to a retracted position, wherein the first electrical contact is positioned on the seat such that the first electrical contact with the seat is biased toward the extended position for biased engagement with the at least one of the instrument adapter or the generator adapter.

Example 16

A surgical device, comprising: (a) a cable configured to communicate an electrical energy therethrough, (b) a first adapter extending from the cable and configured to releasably connect to at least one of an instrument adapter of a surgical instrument or a generator adapter of a generator, the first adapter including: (i) an adapter body, (ii) a first electrical contact electrically connected to the cable, and (iii) an engagement assembly, including: (A) a latch coupling selectively movable relative to the adapter body between a locked position and an unlocked position, wherein the latch coupling in the locked position is configured to capture the at least one of the instrument adapter or the generator adapter for retaining electrical connection between the first electrical contact and the at least one of the instrument adapter or the generator adapter, and wherein the latch coupling in the unlocked position is configured to release the at least one of the instrument adapter or the generator adapter for uncoupling electrical connection between the first electrical contact and the at least one of the instrument adapter or the generator adapter, wherein the latch coupling includes a sleeve operatively connected to the adapter body, wherein the sleeve is biased toward the locked position and configured to selectively move between the locked and unlocked positions, and (B) a communication coupling having a biasing element supported by the adapter body and configured to resiliently bias engagement between the first electrical contact and the at least one of the instrument adapter or the generator adapter for urging contact therebetween.

Example 17

The surgical device of Example 16, wherein the first adapter longitudinally extends along a longitudinal axis, wherein the communication coupling further includes a seat operatively connected to the adapter body and configured to longitudinally move from an extended position to a retracted position, wherein the first electrical contact is positioned on the seat such that the first electrical contact with the seat is biased toward the extended position for biased engagement with the at least one of the instrument adapter or the generator adapter.

Example 18

A method of processing a surgical device, wherein the surgical device includes (a) a cable configured to communicate an electrical energy therethrough, (b) a first adapter extending from the cable and configured to releasably connect to at least one of an instrument adapter of a surgical instrument or a generator adapter of a generator, the first adapter including: (i) an adapter body, (ii) a first electrical contact electrically connected to the cable, and (iii) an engagement assembly, including: (A) a latch coupling selectively movable relative to the adapter body between a locked position and an unlocked position, wherein the latch coupling in the locked position is configured to capture the at least one of the instrument adapter or the generator adapter for retaining electrical connection between the first electrical contact and the at least one of the instrument adapter or the generator adapter, and wherein the latch coupling in the unlocked position is configured to release the at least one of the instrument adapter or the generator adapter for uncoupling electrical connection between the first electrical contact and the at least one of the instrument adapter or the generator adapter, or (B) a communication coupling supported by the adapter body and configured to resiliently bias engagement between the first electrical contact and the at least one of the instrument adapter or the generator adapter for urging contact therebetween, the method comprising: (a) disconnecting the at least one of the at least one of the instrument adapter or the generator adapter from the first adapter; and (b) processing the cable and the first adapter for reuse.

Example 19

The method of Example 18, wherein processing further includes autoclaving the cable and the first adapter for reuse.

Example 20

The method of any one or more of Examples 18 through 19, further comprising selectively moving the latch coupling from the locked position to the unlocked position.

Example 21

A surgical device, comprising: (a) a cable configured to communicate an electrical energy therethrough, (b) a first adapter extending along a longitudinal axis from the cable and configured to releasably connect to at least one of an instrument adapter of a surgical instrument or a generator adapter of a generator, the first adapter including: (i) an adapter body, (ii) a first electrical contact electrically connected to the cable, and (iii) an engagement assembly, including: (A) a latch coupling having a ball-bearing selectively movable relative to the adapter body between a locked position and an unlocked position, wherein the ball-bearing in the locked position is configured to capture the at least one of the instrument adapter or the generator adapter for retaining electrical connection between the first electrical contact and the at least one of the instrument adapter or the generator adapter, and wherein the ball-bearing in the unlocked position is configured to release the at least one of the instrument adapter or the generator adapter for disconnecting electrical connection between the first electrical contact and the at least one of the instrument adapter or the generator adapter, and (B) a communication coupling supported by the adapter body and configured engage the first electrical contact and the at least one of the instrument adapter or the generator adapter for urging contact therebetween.

IV. Miscellaneous

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/854,065, entitled "Method of Reclaiming Portions of Surgical Instruments for Remanufacturing and Sustainability," filed on Jun. 30, 2022, published as U.S. Pub. No. 2024/0006048 on Jan. 4, 2024, the disclosure of which is incorporated by reference herein. Various suitable ways in which the teachings herein may be combined with the teachings of U.S. patent application Ser. No. 17/854,065, will be apparent to those of ordinary skill in the art in view of the teachings herein.

In addition to the foregoing, the teachings herein may be readily combined with the teachings of U.S. patent application Ser. No. 17/854,050, entitled "Surgical Instrument with Predetermined Separation Features for Waste Stream Utilization and Related Methods," filed on Jun. 30, 2022, published as U.S. Pub. No. 2024/0000474 on Jan. 4, 2024, the disclosure of which is incorporated by reference herein. Various suitable ways in which the teachings herein may be combined with the teachings of U.S. patent application Ser. No. 17/854,050 will be apparent to those of ordinary skill in the art in view of the teachings herein.

In addition to the foregoing, the teachings herein may be readily combined with the teachings of U.S. patent application Ser. No. 17/854,641, entitled "Surgical System and Methods of Assembly and Disassembly of Surgical Instrument," filed on Jun. 30, 2022, published as U.S. Pub. No. 2024/0000476, the disclosure of which is incorporated by reference herein. Various suitable ways in which the teachings herein may be combined with the teachings of U.S. patent application Ser. No. 17/854,641 will be apparent to those of ordinary skill in the art in view of the teachings herein.

In addition to the foregoing, the teachings herein may be readily combined with the teachings of U.S. patent application Ser. No. 17/854,104, entitled "Robotic Surgical System with Removable Portion and Method of Disassembling Same," filed on Jun. 30, 2022, published as U.S. Pub. No. 2024/0000526 on Jan. 1, 2024, the disclosure of which is incorporated by reference herein. Various suitable ways in which the teachings herein may be combined with the teachings of U.S. patent application Ser. No. 17/854,104 will be apparent to those of ordinary skill in the art in view of the teachings herein.

In addition to the foregoing, the teachings herein may be readily combined with the teachings of U.S. patent application Ser. No. 17/854,110, entitled "System for Determining Disposal of Surgical Instrument and Related Methods," filed on Jun. 30, 2022, published as U.S. Pub. No. 2024/0001416 on Jan. 1, 2024, the disclosure of which is incorporated by reference herein. Various suitable ways in which the teachings herein may be combined with the teachings of U.S. patent application Ser. No. 17/854,110 will be apparent to those of ordinary skill in the art in view of the teachings herein.

In addition to the foregoing, the teachings herein may be readily combined with the teachings of U.S. patent application Ser. No. 17/854,114, entitled "Reclamation Packaging for Surgical Instrument and Related Methods," filed on Jun. 30, 2022, published as U.S. Pub. No. 2024/0000491 on Jan. 1, 2024, the disclosure of which is incorporated by reference herein. Various suitable ways in which the teachings herein may be combined with the teachings of U.S. patent application Ser. No. 17/854,114 will be apparent to those of ordinary skill in the art in view of the teachings herein.

In addition to the foregoing, the teachings herein may be readily combined with the teachings of U.S. patent application Ser. No. 17/854,120, entitled "Surgical Instrument with Various Alignment Features and Methods for Improved Disassembly and Assembly," filed on Jun. 30, 2022, published as U.S. Pub. No. 2024/0000475 on Jan. 1, 2024, the disclosure of which is incorporated by reference herein. Various suitable ways in which the teachings herein may be combined with the teachings of U.S. patent application Ser. No. 17/854,120 will be apparent to those of ordinary skill in the art in view of the teachings herein.

In addition to the foregoing, the teachings herein may be readily combined with the teachings of U.S. patent application Ser. No. 17/854,127, entitled "Surgical System and Methods for Instrument Assessment and Cleaning," filed on Jun. 30, 2022, published as U.S. Pub. No. 2024/0003820 on Jan. 1, 2024, the disclosure of which is incorporated by reference herein. Various suitable ways in which the teachings herein may be combined with the teachings of U.S. patent application Ser. No. 17/854,127 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical device, comprising:
   (a) a cable configured to communicate an electrical energy therethrough,
   (b) a first adapter extending along a longitudinal axis from the cable and configured to releasably connect to at least one of an instrument adapter of a surgical instrument or a generator adapter of a generator, the first adapter including:
      (i) an adapter body,
      (ii) a first electrical contact electrically connected to the cable, and
      (iii) an engagement assembly, including:
         (A) a latch coupling having a latch portion selectively movable relative to the adapter body between a locked position and an unlocked position, wherein the latch portion includes at least lease one catch member angularly surrounding at least a majority of the longitudinal axis or a sleeve rotatable about the longitudinal axis, wherein the latch portion in the locked position is configured to capture the at least one of the instrument adapter or the generator adapter for retaining electrical connection between the first electrical contact and the at least one of the instrument adapter or the generator adapter, and wherein the latch portion in the unlocked position is configured to release the at least one of the instrument adapter or the generator adapter for uncoupling electrical connection between the first electrical contact and the at least one of the instrument adapter or the generator adapter, or
         (B) a communication coupling supported by the adapter body and configured to resiliently bias engagement between the first electrical contact and the at least one of the instrument adapter or the generator adapter for urging contact therebetween.

2. The surgical device of claim 1, further comprising a surgical instrument having an instrument adapter or a generator having a generator adapter.

3. The surgical device of claim 1, wherein the first adapter includes the latch coupling.

4. The surgical device of claim 3, wherein the latch coupling includes the sleeve operatively connected to the adapter body, wherein the sleeve is configured to translate between the locked and unlocked positions.

5. The surgical device of claim 4, wherein the latch coupling further includes a latch biasing element, wherein the latch biasing element resiliently biases the sleeve toward the locked position.

6. The surgical device of claim 3, wherein the latch coupling further includes the at least one catch member positioned about the longitudinal axis and movable in a radial direction relative to the longitudinal axis and configured to longitudinally capture the at least one of the instrument adapter or the generator adapter in the locked position and further configured to longitudinally release the at least one of the instrument adapter or the generator adapter in the unlocked position.

7. The surgical device of claim 6, wherein the at least one catch member includes a plurality of ball bearings.

8. The surgical device of claim 3, wherein the latch coupling includes the sleeve operatively connected to the adapter body, wherein the sleeve is configured to rotate between the locked and unlocked positions.

9. The surgical device of claim 8, wherein the latch coupling further includes a bayonet coupling having a bayonet slot, wherein the bayonet slot extends through at least one of the sleeve or the adapter body.

10. The surgical device of claim 9, wherein the bayonet slot extends through the sleeve.

11. The surgical device of claim 10, wherein the latch coupling further includes a latch biasing element, wherein the latch biasing element resiliently biases the sleeve toward the locked position.

12. The surgical device of claim 3, wherein the first adapter includes the communication coupling.

13. The surgical device of claim 1, wherein the first adapter includes the communication coupling.

14. The surgical device of claim 13, wherein the communication coupling has a biasing element supported by the adapter body and configured to resiliently bias engagement between the first electrical contact and the at least one of the instrument adapter or the generator adapter for urging contact therebetween.

15. The surgical device of claim 14, wherein the communication coupling further includes a seat operatively connected to the adapter body and configured to longitudinally move from an extended position to a retracted position, wherein the first electrical contact is positioned on the seat such that the first electrical contact with the seat is biased toward the extended position for biased engagement with the at least one of the instrument adapter or the generator adapter.

16. A surgical device, comprising:
 (a) a cable configured to communicate an electrical energy therethrough,
 (b) a first adapter extending from the cable and configured to releasably connect to at least one of an instrument adapter of a surgical instrument or a generator adapter of a generator, the first adapter including:
  (i) an adapter body,
  (ii) a first electrical contact electrically connected to the cable, and
  (iii) an engagement assembly, including:
   (A) a latch coupling selectively movable relative to the adapter body between a locked position and an unlocked position, wherein the latch coupling in the locked position is configured to capture the at least one of the instrument adapter or the generator adapter for retaining electrical connection between the first electrical contact and the at least one of the instrument adapter or the generator adapter, and wherein the latch coupling in the unlocked position is configured to release the at least one of the instrument adapter or the generator adapter for uncoupling electrical connection between the first electrical contact and the at least one of the instrument adapter or the generator adapter, wherein the latch coupling includes a sleeve operatively connected to the adapter body, wherein the sleeve is biased toward the locked position and configured to selectively move between the locked and unlocked positions, and
   (B) a communication coupling having a biasing element supported by the adapter body and configured to resiliently bias engagement between the first electrical contact and the at least one of the instrument adapter or the generator adapter for urging contact therebetween.

17. The surgical device of claim 16, wherein the first adapter longitudinally extends along a longitudinal axis, wherein the communication coupling further includes a seat operatively connected to the adapter body and configured to longitudinally move from an extended position to a retracted position, wherein the first electrical contact is positioned on the seat such that the first electrical contact with the seat is biased toward the extended position for biased engagement with the at least one of the instrument adapter or the generator adapter.

18. A method of processing a surgical device, wherein the surgical device includes (a) a cable configured to communicate an electrical energy therethrough, (b) a first adapter extending from the cable and configured to releasably connect to at least one of an instrument adapter of a surgical instrument or a generator adapter of a generator, the first adapter including: (i) an adapter body, (ii) a first electrical contact electrically connected to the cable, and (iii) an engagement assembly, including: (A) a latch coupling selectively movable relative to the adapter body between a locked position and an unlocked position, wherein the latch coupling in the locked position is configured to capture the at least one of the instrument adapter or the generator adapter for retaining electrical connection between the first electrical contact and the at least one of the instrument adapter or the generator adapter, and wherein the latch coupling in the unlocked position is configured to release the at least one of the instrument adapter or the generator adapter for uncoupling electrical connection between the first electrical contact and the at least one of the instrument adapter or the generator adapter, or (B) a communication coupling supported by the adapter body and configured to resiliently bias engagement between the first electrical contact and the at least one of the instrument adapter or the generator adapter for urging contact therebetween, the method comprising:
 (a) disconnecting the at least one of the at least one of the instrument adapter or the generator adapter from the first adapter; and
 (b) processing the cable and the first adapter for reuse.

19. The method of claim 18, wherein processing further includes autoclaving the cable and the first adapter for reuse.

20. The method of claim 18, further comprising selectively moving the latch coupling from the locked position to the unlocked position.

* * * * *